United States Patent [19]

Jenkins

[11] Patent Number: 5,055,108
[45] Date of Patent: Oct. 8, 1991

[54] APPLIANCE FOR MAINTAINING MOISTURE IN THE MOUTH

[76] Inventor: E. Preston Jenkins, 9533 Clement Rd., Silver Spring, Md. 20910

[21] Appl. No.: 528,875
[22] Filed: May 25, 1990
[51] Int. Cl.⁵ ............................................ A61M 31/00
[52] U.S. Cl. .................................... 604/54; 604/285; 606/234
[58] Field of Search ............... 604/285, 286, 304, 307, 604/54, 246, 247; 433/167, 168.1; 606/234, 235, 236

[56] References Cited

U.S. PATENT DOCUMENTS

| 3,219,033 | 11/1965 | Wallshein . | |
|---|---|---|---|
| 3,610,248 | 10/1971 | Davidson | 606/236 |
| 3,875,940 | 4/1975 | Beuther | 606/234 X |
| 3,991,471 | 11/1976 | Hoops . | |
| 4,020,844 | 5/1977 | Vickery | 604/54 |
| 4,838,882 | 6/1989 | Molinoff | 604/286 |
| 4,917,674 | 4/1990 | Molinoff | 604/54 X |

OTHER PUBLICATIONS

Publication: "Why Don't Dentists See Dry Mouth in Patients?", 4AGD Impact, Oct. 1989, pp. 4, 5 and 8.

Primary Examiner—John D. Yasko
Attorney, Agent, or Firm—Howard L. Rose

[57] ABSTRACT

The invention is to a liquid filled soft pouch attached to an upper partial or complete denture or a Hawley appliance for moisturizing a dry mouth (Xerostomia) the pouch having a fill valve and an exit valve, the latter operated by the tongue to permit exit of liquid, artifical salvia, to wet the mouth. The exit valve may be eliminated by employing a lower surface of the pouch which is porous so that it in effect sweats and liquid may be acquired by running the tongue over the porous surface.

7 Claims, 1 Drawing Sheet

APPLIANCE FOR MAINTAINING MOISTURE IN THE MOUTH

The present invention relates to alleviating the symptoms of dry mouth (Xerostomia) and more particularly to an appliance fitted in the mouth to provide a flow of fluid as required to maintain the mouth moist.

BACKGROUND OF THE INVENTION

As stated in the October 1989 issue of AGD Impact at page 4, "Dry mouth is unexplored territory for dentists, yet it haunts about one-third of all adult patients." Dry mouth may produce "pain, a burning sensation of the tongue, difficulty chewing and swallowing foods, . . ."

Two U.S. patents directed to the problem of dry mouth are U.S. Pat. Nos. 4,838,882 and 3,991,471. The former patent provides a pad or sponge contained in a knit cotton cloth that is saturated with water and placed in a cheek pouch of the user. Such an arrangement puffs out the cheek, is uncomfortable, unsanitary and liquid flow is not readily controlled. Further, such a pouch will interfere with chewing and, thus, must be removed while eating.

The latter patent provides a palatal appliance for maintaining humidity in the mouth and respiratory tract. It comprises a rigid plastic shell that conforms to the hard palate and holds a sponge saturated with liquid. Again, the discharge of liquid from the device is substantially uncontrolled and the device must be removed during eating.

BRIEF DESCRIPTION OF THE PRESENT INVENTION

The appliance of the present invention may be affixed to a full or partial upper denture or supported by natural teeth or a Hawley appliance and essentially comprises a soft pouch disposed adjacent the hard palate having two valves, one for filling the pouch and one for discharging liquid from the pouch in response to action of the tongue. In the latter case, the valve may be such as to be moved (opened) by the tongue or may be opened by pressure developed by the tongue pressing on the pouch. Thus, during eating or speaking or at other times selected by the user the appropriate use of the tongue permits escape of small quantities of liquid from the pouch into the mouth or more specifically, onto the tongue or into food.

In a second embodiment of the appliance, the discharge valve is eliminated and the lower surface of the pouch is composed of a liquid permeable membrane having pores of a size such that the surface in effect, sweats. The pores are of such size as not to hold food and, thus, the appliance does not require removal while eating, so that by slight suction or movement of the tongue across the membrane, liquid is made available to the tongue and thus the mouth.

The appliance thus provided is small, pliable and, thus, comfortable and permits controlled flow of liquid into the mouth and also of great importance, permits the appliance to be filled without removal from the mouth if necessary. This latter feature results from the fact that a small plunger operated liquid filled tube may be inserted into the fill valve, which may also be of the type used to inflate a football, and upon operation of the plunger inject liquid into the pouch.

The liquid would normally constitute artificial saliva and may include small quantities of fluorine to reduce cavities.

OBJECTS OF THE INVENTION

It is, thus, an object of the present invention to provide a comfortable appliance for insertion in the mouth of a patient suffering from Xerostomia from which appliance liquid flow is to a great extent under control of the user.

Another object of the present invention is to provide a soft pouch for holding liquid which pouch may be secured in the mouth of an individual and provide controllable flow of liquid into the user's mouth.

Still another object of the present invention is to provide a pouch insertable into an individual's mouth which may be filled with liquid in situ but may be readily removed for fitting.

DETAILED DESCRIPTION OF THE INVENTION

Figure 1:
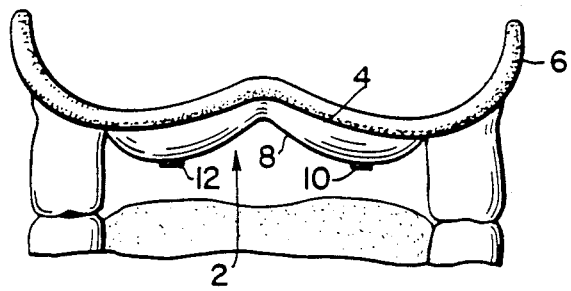
FIG. 1 is a view in elevation of a first embodiment of the present invention.
Figure 2:
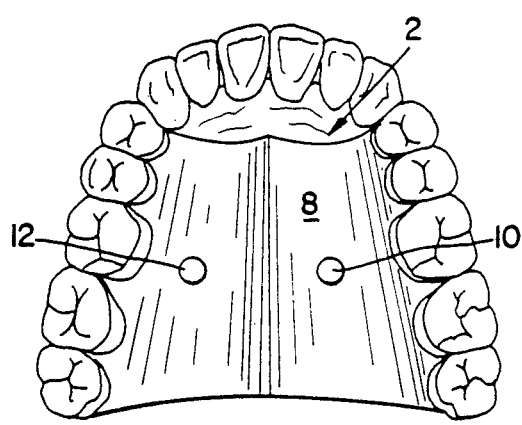
FIG. 2 is a bottom view of the appliance of FIG. 1.

Referring now specifically to FIGS. 1 and 2 of the accompanying drawings, a soft plastic pouch 2 is secured along its upper surface 4 to base 6 of a denture or a Hawley appliance. In the latter case, the tooth braces are omitted from the appliance. The pouch may be secured to the base by chemical bonding or other suitable means.

The pouch 2 may be fabricated from methyl methocrylate and has disposed in its lower wall 8 two valves, an intake valve 10 for filling the pouch with liquid and an outlet valve 12 for permitting, when opened, flow of liquid into the mouth.

Figure 3:
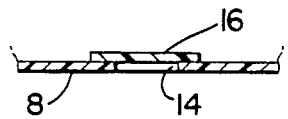
FIG. 3 is a detailed view of the inlet valve of FIG. 1.

The valve 10, see FIG. 3, may be a flap valve secured to the interior of the wall 8 of the pouch 2 and includes an opening 14 in the wall 8 and a stiff plastic flap 16 secured by bonding or chemically to the one side of and completely covering the opening 14. A spring biased valve may also be employed.

Figure 4:
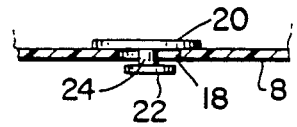
FIG. 4 is a detailed view of an outlet valve of FIG. 1.

The valve 12 may be similar to valve 10 and is illustrated in FIG. 4 of the accompanying drawings. The valve 12 cooperates with a hole 18 in the lower wall 8 of the pouch 2. Interiorly of the pouch the hole 18 is covered by a stiff piece of flat plastic 20 anchored on the inner surface of the lower wall 8 thereby sealing the hole. A small thin flat member 22 is located below the wall 8 generally parallel to the flat plastic member 20 and is connected thereto by a stem 24. Upward pressure on the member 22 unseated the flap 20 and permits liquid to flow by it into the mouth.

Figure 5:
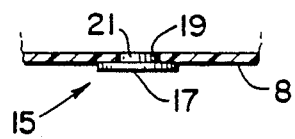
FIG. 5 is a detailed view of another outlet valve.

Another form of outlet valve that may be employed is illustrated in FIG. 5. Essentially this valve, generally designed by reference numeral 15 includes a piece of stiff plastic 17 closing a hole 19 in wall 8. Normal position for the plastic member 17 is tight against the wall 8 and it may have a pluglike member 21 extending into hole 19 to further help seal the opening. The valve is opened in this embodiment by pressing the tongue against the pouch 2 to pressurize the liquid and force the valve 15 open. The degree of pressure determines the quantity of liquid discharged.

Obviously, other valve arrangements may be employed for both of the valves 10 and 12, those illustrated indicating several that may be used.

The appliance of FIGS. 1 and 2 is illustrated as applied to a denture which may be a full or partial denture. In the event that the user does not have a denture, the appliance may be secured to a Hawley appliance or snap-on clips or related devices may be used to attach the pouch 2 to the teeth of the wearer. Such latter devices are shown in the aforesaid U.S. Pat. No. 3,991,471.

Figure 6:
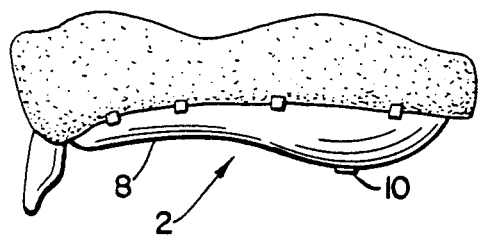
FIG. 6 is a view in elevation of a second embodiment of the invention.

In the device of FIG. 6, the valve 12 is eliminated and the lower wall 8 of the pouch 2 is a porous member of such porosity as to maintain the outer surface of the wall 8 wet in effect sweating so that as the tongue rubs against the wall it picks up moisture as does food as it contacts the surface. The pores, however, are small enough that food will not enter them and clog the appliance.

I claim:

1. A flexible, hollow pouch inflatable with liquid for selectively suppling liquid to the mouth of the user comprising
   means for filling said pouch with liquid,
   means for securing the pouch immediately adjacent the hard pallet, and
   means responsive to movement of the tongue for dispensing liquid from the pouch.

2. A flexible, hollow pouch according to claim 1 wherein
   said means responsive to movement of the tongue is a pressure sensitive valve.

3. A flexible, hollow pouch according to claim 2 wherein
   said pressure sensitive valve is actuated by the tongue of the user pressing against the valve.

4. A flexible, hollow pouch according to claim 2 wherein
   said pressure sensitive valve is actuated by pressure developed in the liquid as a result of pressing the tongue against the pouch.

5. A flexible, hollow pouch according to claim 1 wherein
   said pouch is secured to a partial or complete denture.

6. A flexible, hollow pouch according to claim 1 further comprising
   a Hawley appliance, and
   means for securing said pouch to the Hawley appliance.

7. A flexible, hollow pouch according to claim 1 wherein means for dispensing comprises
   a porous lower member of said pouch having a surface of a porosity such that the surface of said member remains moist and does not drip liquid.

* * * * *